United States Patent [19]

Strasberg et al.

[11] Patent Number: 5,200,398
[45] Date of Patent: Apr. 6, 1993

[54] COMPOSITION FOR THE PRESERVATION OF ORGANS COMPRISING GLUCURONIC ACID OR A PHYSIOLOGICALLY TOLERATED SALT OR ESTER THEREOF

[75] Inventors: Steven M. Strasberg, Toronto; Robert P. C. Harvey, Oakville, both of Canada

[73] Assignee: Mount Sinai Hospital Corporation, Toronto, Canada

[21] Appl. No.: 759,567

[22] Filed: Sep. 12, 1991

[51] Int. Cl.$^5$ ............... A61K 9/08; A61K 31/715; A01N 1/02
[52] U.S. Cl. ........................... 514/23; 514/60; 514/832; 514/893; 514/894; 435/1
[58] Field of Search ............... 514/23, 60, 832, 893, 514/894; 435/1

[56] References Cited

U.S. PATENT DOCUMENTS

| | | | |
|---|---|---|---|
| 4,798,824 | 1/1989 | Belzer et al. | 514/832 |
| 4,870,071 | 9/1989 | Ogata et al. | 514/562 |
| 4,873,230 | 10/1989 | Belzer et al. | 514/832 |
| 4,879,283 | 11/1989 | Belzer et al. | 514/832 |
| 4,898,890 | 2/1990 | Sato et al. | 514/685 |
| 4,920,044 | 4/1990 | Bretan | 435/2 |
| 4,959,358 | 9/1990 | Carey et al. | 514/37 |
| 5,082,831 | 1/1992 | Leaf et al. | 514/60 |

OTHER PUBLICATIONS

Jamieson, N. V. et al, Transplantation 46:512–516, Oct. 1988.
Southard, J. H. and Belzer, F. O, Cryobiology 17:540–548 (1980).
Mees, N. et al, J. Trauma 22:118–120 (1982).
Iu, S. et al, Transplantation, 44:562–569 (1987).
McKeown, C. M. B. et al, Transplantation, 46:178–191 (1988).
Holloway, C. M. B. et al, Transplantation 48:179–188 (1989).
Holloway, C. M. B. et al, Transplantation 49:225–229 (1990).
Southard et al Transplantation 49:251–257 (1990).
Wicomb, W. N. et al, Transplantation 49:261–264 (1990).
Jamieson, N. V. et al, Transplantation Proc. 21:1294–1295 (1989).
Ploeg, R. J. et al, Transplantation Proc. 21:1378–1380 (1989).
Jamieson, N. V. et al, Cryobiology 25:300–310 (1988).
Hoffman, R. M. et al, Arch. Surg. 118:919–921 (1983).
Olthoff, K. M. et al, Transplantation 49:284–290 (1990).
Harvey, P. R. C. et al Clinica. Chimica. Acta. 180:203–212 (1989).
Harvey, P. R. C. et al. Transplantation 45:1016–1020 (1988).
Belzer, F. O. and Southard J. M., Transplantation 45:673–676 (1988).
McAnulty, J. F. et al, Transplantation Proc. 19:1376–1379 (1987).
Belzer, F. O. Transplantation Proc. 9:1543–1546 (1977).

*Primary Examiner*—Ronald W. Griffin
*Attorney, Agent, or Firm*—Bereskin & Parr

[57] ABSTRACT

A novel composition for the preservation of organs intended for transplantation and a method of preserving organs intended for transplantation using the composition are described. The composition contains glucuronic acid or a physiologically tolerated salt or ester thereof in a pharmaceutically acceptable organ preservation solution.

15 Claims, 11 Drawing Sheets

COMPOSITION FOR THE PRESERVATION OF ORGANS COMPRISING GLUCURONIC ACID OR A PHYSIOLOGICALLY TOLERATED SALT OR ESTER THEREOF

BACKGROUND OF THE INVENTION

The present invention relates to a composition for the preservation of organs intended for transplantation and a method of preserving organs intended for transplantation using the composition.

Transplantation of organs is now considered to be a definitive treatment for patients with end stage liver, kidney, heart and pancreas disease. There is thus a great deal of interest in improving ex vivo storage of cadaveric organs and thus the viability of organ transplants.

The two most commonly used methods for organ preservation are hypothermic storage and continuous pulsatile perfusion. With hypothermic storage, the organs are rapidly cooled immediately after removal from the cadaver donor using a combination of external cooling and a short period of perfusion. The hypothermic storage method is a preferred method due to its practicality and the ease of transportation of the organs. Continuous pulsatile perfusion involves hypothermic pulsatile perfusion after flushing with a chilled electrolyte solution.

A number of organ preservation solutions have been developed with a view to extending organ preservation time. Ringer's lactate and isotonic saline solutions have been used as extracellular flushing solutions and have been reported to allow for safe renal preservation for short periods of time, i.e. up to four hours. Storage for longer periods of time may result in severe histologic ischemic damage and subsequent non-function of the organs (column 5, U.S. Pat. No. 4,920,004)

An intracellular electrolyte solution developed by Collins et al., (Lancet 2:1219, 1969), has been reported to offer several advantages for hypothermic storage. Table I shows the composition of the Collins solution which is most commonly used. Modified Collins' solutions have also been developed for use in hypothermic storage. For example, Euro-collins solution is similar to Collins solution with the exception that it does not contain magnesium.

Other organ preservation solutions which have been developed include Sacks' solutions ($S_1$ and $S_2$) which have high intracellular ion concentration and osmotic pressure (Sacks, S. A., Lancet 1:1024, 1973). Table I shows the composition of the Sacks-2 flush solution. The solutions have been reported to provide improved transplantation results after storage of kidneys for up to 72 hours.

Protective additives such as ATP-$MgCl_2$, AMP-$MgCl_2$ and inosine have also been included in preservation/flush solutions. (Siegel, N. J. et al., Am. J. Physiol. 245:F530, 1983: Stromski, M. E. et al, Am. J. Physiol. 250:F834, 1986; Sumpio, B. E. et al., Am. J. Physiol. 247:R1047; Stromski, M. E. et al., Am J. Physiol, 250:F834, 1986). Belzer et al., (Transpl. Proc. 16:161, 1984) developed a perfusate containing ATP-$MgCl_2$ (see Table I for ingredients) but it has not been used for simple cold storage (Arch. Surg. 122:790–794, 1987).

U.S. Pat. No. 4,920,004 discloses a hyperosmotic intracellular flush and storage solution that is reported to combine the salient features of Belzer's ATP-$MgCl_2$ perfusat commonly used Collins' C-2 Flush solutions. Mannitol is substituted in place of dextrose in Collins. C-2 solution and adenosine and magnesium are added to the solution to improve the preservation properties of the flush solution.

U.S. Pat. Nos. 4,798,824 and 4,873,230 disclose solutions for the preservation of organs (particularly kidneys) prior to implantation, containing a specific synthetic hydroxyethyl starch in place of serum albumin to produce the required oncotic pressure. In particular, U.S. Pat. No. 4,798,824 discloses a solution including 5% hydroxyethyl starch having a molecular weight of from about 200,000 to about 300,000 and wherein the hydroxyethyl starch is substantially free of ethylene glycol, ethylene chlorohydrin, sodium chloride and acetone. U.S. Pat. No. 4,873,230 discloses a solution containing hydroxyethyl starch having a molecular weight of from about 150,000 to about 350,000 daltons, a degree of substitution of from about 0.4 to about 0.7 and being substantially free of ethylene glycol, ethylene chlorohydrin, sodium chloride and acetone.

Marshall's isotonic citrate solution (Table I) has been reported to be capable of prolonging the period of safe hypothermic organ storage. It contains the impermeant anion, citrate and other substances which are believed to prevent free radical injury.

U.S. Pat. No. 4,879,283, discloses a solution for the preservation of organs which contains lactobionate and raffinose and has a solution osmolality of about 320 mOsm/L, $K^+$ of 120 mM and $Na^+$ of 20 mM. The solution also contains a synthetic hydroxyethyl starch and other components such as glutathione and adenosine. The solution disclosed in U.S. Pat. No. 4,879,283 is commonly known as the University of Wisconsin solution or UW solution and its composition is shown in Table I. The solution has been reported to successfully preserve the liver (Jamieson, N. V. et al., Transplantation 46:517, 1988), kidney (Ploeg, R.J. et al., Transplantation 46:191, 1988), and pancreas (Wahlberg, J. A., Transplantation, 43:5, 1987). Preliminary animal studies suggest that the solution may also be effective for the preservation of the heart (Wicomb, W. N., Transplantation 47:733, 1988; and Swanson, D. K., J. Heart Transplant 7:456, 1988).

The UW solution and Marshall's isotonic citrate solution are believed to provide improved organ preservation as a result of their ability to prevent cell swelling or oxygen free radical-mediated injury (Belzer, F. O. and Southard, J. H., In: Transplantation: Approaches to Graft Rejection. N.Y.,: List, 291, 1986; Toledo-Pereyra, L. H. et al, Ann. Surg. 181:289, 1975; Downes, G. et al, Transplantation 16:46, 1973; and Green, G. S. Pegg, D. E., In: Pegg, D. E., Jacobson, J. A., eds. Organ preservation. Edinburgh: Churchill Livingstone, 86, 1979). The solutions contain impermeant anions, citrate or lactobionate, which are added to maintain the normal double-Donnan equilibrium and prevent cell swelling in spite of the inactivation of the Na/K ATPase - dependent pump by hypothermia (Belzer, F. O. and Southard, J. H., In: Transplantation: Approaches to Graft Rejection. N.Y.: Liss, 291, 1986; Martin D. R. et al, Ann Surg 175:111, 1972; Southard, J. H. and Belzer, F. O. Cryobiology 17:540, 1980; and Mees N. et al., J. Trauma 22:118, 1982).

The present inventors have studied the relationship between transplant viability and liver function. In particular, the present inventors using a rat liver model have found that AST (aspartate aminotransferase) and LDH (lactate dehydrogenase) concentration in perfusate, discriminated between viable and nonviable livers across as well as within preservation groups. AST was found to give the best separation between viable and nonviable livers. Functions such as ALT (alanine aminotransferase) concentration in perfusate were found to separate viable from nonviable liver allografts only within preservation groups. In studying markers of allograft viability, the present inventors observed that rat livers stored at 1° C. for 4 hours or at 37° C. for 1 hour in a simple preservation solution (NaCl 0.9%, $CaCl_2$, 2 mM) were all viable on transplantation but those stored at 4° C. for 8 hours or at 37° C. for 2 hours were nonviable. Cold preserved nonviable livers were also shown to have increased vascular resistance, platelet trapping and an initially low, but then high rise in AST upon reperfusion, all suggesting injury to the microcirculation. (Iu, S. et al, Transplantation, 44:562, 1987).

The present inventors have further identified the morphological changes that occur in livers stored for the above-mentioned critical times using light and electron microscopy after perfusion fixation. (McKeown, C. M. B. et al., Transplantation, 46:178, 1988). The present inventors observed that reversible injury was manifest by partial disruption of the endothelium and swelling of sinusoidal lining cells; hepatocytes appeared essentially normal, apart from some minor bleb formation. Irreversible injury and loss of viability was characterized by a completely deficient endothelium; lining cells were round with dark nuclei, and were detached from the underlying hepatocytes.

The present inventors also compared the effects on the microcirculation of preservation in UW and Marshall's solution and other control solutions and concluded that injury to the microcirculation was due neither to free-radical-mediated injury nor to cell swelling (Holloway, C.M.B. et al., 48, 179, 1989).

SUMMARY OF THE INVENTION

The present inventors have found that inclusion of glucuronate in a preservation solution for use in the preservation of an organ intended for transplantation provides improved organ preservation properties over other known preservation solutions. In particular, the present inventors have found that solutions containing glucuronate provided superior protection of the microcirculation when compared to solutions based on non-carbohydrate or other carbohydrate anions in histologic studies of liver allografts. Further, results of liver function tests demonstrated that liver allografts preserved in a preservation solution including glucuronate have greater transplantation viability than allografts preserved in UW solution. Preservation solutions including glucuronate may accordingly extend the preservation time of an organ permitting increased organ availability and sharing and decreased organ wastage which would necessarily result in reduced transplantation costs. The use of a preservation solution including glucuronate may also provide better preservation quality for short term storage (i.e. <30 hours).

The present invention therefore provides a composition for the preservation of an organ intended for transplantation comprising glucuronic acid or a physiologically tolerated salt or ester thereof in a pharmaceutically acceptable organ preservation solution. Preferably the pharmaceutically acceptable organ preservation solution has substantially the composition of UW solution and most preferably is a modified UW solution devoid of lactobionate.

The invention also relates to a method for preserving an organ intended for transplantation in a subject comprising infusing said organ with a composition comprising glucuronic acid or a physiologically tolerated salt or ester thereof in a pharmaceutically acceptable organ preservation solution. Preferably the pharmaceutically acceptable organ preservation solution has substantially the composition of UW solution and most preferably is a /modified UW solution devoid of lactobionate.

DESCRIPTION OF THE DRAWINGS

The invention will now be described in relation to the drawings in which.

DETAILED DESCRIPTION OF THE INVENTION

Figure 1:
FIG. 1 is a photomicrograph of a section of a normal rat liver (original magnification x 400, H and E stain)

As hereinbefore mentioned, the present invention relates to a composition for the preservation of organs intended for transplantation comprising glucuronic acid or a physiologically tolerated salt or ester thereof in a pharmaceutically acceptable organ preservation solution. The composition of the invention has improved organ preservation properties over previously known preservation solutions.

The terms "preservation", "preserving" or "infusing" used herein include but are not limited to perfusion, flushing and storage of an organ intended for transplantation.

The pharmaceutically acceptable organ preservation solution used in the composition of the invention may be any commonly used preservation solution. The ingredients of exemplary commonly used preservation solutions are set forth in Table I. Preferably the preservation solution has substantially the composition of UW solution (see Table II) and most preferably is a modified UW solution devoid of lactobionate and containing glucuronate in an equimolar dose.

The glucuronic acid or a physiologically tolerated salt or ester thereof used in the composition of the invention may be obtained using the methods described by Mehltretter (Advan. Carbohydrate Chemistry, 8:231, 1953) or may be obtained commercially (for example, from Sigma Chem. Co., St. Louis, Mo., U.S.A.). The compounds that may be used in the composition of the invention include glucuronic acid, sodium glucuronate, potassium glucuronate and other soluble glucuronate salts or esters. The concentration of the glucuronic acid or a physiologically tolerated salt or ester thereof in the composition of the invention may be from about 3 to 200 mM, preferably about 100 to 140 mM, most preferably 100 mM.

In a preferred embodiment of the invention, the composition includes but is not limited to the components set out in Table II herein.

In a particularly preferred embodiment of the invention the composition comprises 100 mM glucuronate (as sodium or potassium salt) 25 mM KH$_2$PO$_4$, 5 mM MgSO$_4$, 30 mM raffinose, 5 mM adenosine, 3 mM glutathione, 1 mM allopurinol, 50 g/l hydroxyethyl starch, 100 U/l insulin, 0.5 ml/l bactrim, and 8 mg/l dexamethasone. The composition of the invention may be prepared by mixing the various components of the composition using conventional methods. In particular, the various components of the composition of the invention may be mixed in a liter of distilled water to produce the overall composition. The preferred composition of the invention may be prepared according to the constituent ranges set forth herein in Table II or according to the preferred amounts set forth above.

The solution may be brought to a pH of about 6.8 to 7.6, preferably 7.2, at 25° C. with NaOH. The ratio of Na$^+$ to K$^+$ in the resulting composition may be about 150:3.5 to 20:140, preferably 30:120 which is the ratio of these ions in UW solution. Osmolality of the resulting solutions may be adjusted to about 300±30 mOsm/l using, if desired, variable concentrations of mannitol.

The invention also relates to enhanced embodiments of the composition of the invention which include the composition described above containing other additives. Examples of such additives are enzyme inhibitors (e.g. 2'-deoxycoformycin), buffers (KHCO$_3$) and calcium entry blockers.

The present invention also contemplates a method for preserving an organ intended for transplantation through the use of the composition described above. In particular, an organ such as a liver, may be flushed during harvesting and after its removal from the donor with a composition of the invention. The organ is then stored in a composition of the invention under hypothermic conditions. Alternatively, after initial flushing, the organ may be connected to a pump wherein a cold perfusate of the composition of the invention is continuously circulated through the organ. Prior to transplantation the organ may be flushed again with the composition of the invention.

The method of the invention may be used to preserve any organ intended for transplantation, preferably an intraabdominal organ such as the liver, pancreas and kidney, most preferably the liver.

The following non-limiting examples are illustrative of the present invention:

EXAMPLE 1

A variety of preservation solutions based on different anions, both carbohydrate and noncarbohydrate, were tested for their efficacy in protection of the microcirculation using morphologic criteria. In particular livers stored in preservation solutions based on carbohydrate and noncarbohydrate anions were compared with livers stored in saline and isotonic citrate, and with each other. Comparisons of solutions containing different carbohydrate anions were also made to identify the anion that provided the best preservation of the microcirculation. To evaluate the importance of hydroxylation of the anion, livers stored in solutions based on butyrate, α-hydroxybutyrate, and γ-hydroxybutyrate were also compared. The latter two compounds have a similar carbon backbone to citrate and have hydroxyl groups at carbons 2 and 4 respectively; butyrate is not hydroxylated and was used as a control.

The detailed composition of each preservation solution tested is shown in Table III. Predominantly univalent anions were used at a concentration of 100 mM, the same concentration of lactobionate in UW solution (Jamieson, N.V. et al, Transplantation 46:517, 1988). Reduced concentrations of divalent anions were employed. Most solutions contained 5 mM MgSO$_4$ although some otherwise identical solutions with 40 mM MgSO$_4$ were employed to evaluate the efficacy of high or low concentrations of magnesium. Osmolality was kept constant in all solutions at 300±3 mOsm/l, using variable concentrations of mannitol. The pH of all solutions was brought to 7.4 at 25° C. with NaOH.

Where possible, the ratio of Na+ to K+ in the test preservation solutions was 45:54 which is the ratio of these ions in isotonic citrate solution. For anions not available as the K+ salt or free acid, only the sodium salt was used.

The following techniques were used in evaluating the preservation solutions:

Livers were harvested from male Wistar rats (200–300 g), using the method for donor hepatectomy described by Kamada, N. and Calne, R. Y., Transplantation 28:47, 1979, and Transplantation 93:64, 1983. All livers were flushed in situ with 12 cc of the test preservation solution to be tested with 500 i.u. heparin, followed by 20 cc of the preservation solution alone, then stored in the preservation solutions to be tested.

Livers preserved in the solutions to be tested were stored for 8 hours at 4° C. and were compared to the appearance of livers preserved in saline or isotonic citrate for the same time period. If the appearance was more comparable to the latter, the experiment was repeated using a 16 hour storage time.

Following preservation, perfusion-fixation was preformed as described in McKeown, C.M.B. et al, 1988, Transplantation, 46:178. Specimens were then embedded in paraffin, sectioned, and stained with hematoxylin and eosin. All slides were blinded prior to examination, and assigned a qualitative and descriptive evaluation. To assist comparison of livers stored in different solutions, sections were scored on a scale of 0 to 8. A score of 0 described a liver with the appearance of unpreserved controls; 4 represented the appearance associated with the limits of viability, and 8 the appearance associated with lethal preservation injury, based on saline-stored controls described in McKeown, C. M. B. et al, Transplantation, 46:178, 1988.

Solutions associated with livers having a score of 4 or less, that is, a histologic appearance compatible with viability after 8 hours storage, were considered superior solutions.

A. Comparison of Solutions Containing Carbohydrate v. Noncarbohydrate Anions

Livers stored in solutions based on propionate or butyrate and its hydroxyl derivatives or isothionate, i.e. non carbohydrates (Table III) were compared with livers stored in solutions based on galacturonate, gluconate, 9lucoheptonate, saccharate, glucuronate, and lactobionate (Table III) i.e. carbohydrates. Several glucuronate, lactobionate and gluconate solutions were tested. In these solutions the amounts of sodium and potassium salts of these substances as well as the amount of MgSO4 was varied according to the specific formulae outlined in Table III. Livers preserved in solutions containing either a 5 mM or 40 mM concentration of MgSO4 were histologically indistinguishable.

Figure 2:
FIG. 2 is a photomicrograph of a section of a rat liver allograft stored for 8 hours at 1° C. in solutions containing normal saline and 2 mM calcium chloride (original magnification ×400, H and E stain)

The photomicrographs of sections of rat liver allografts stored in the noncarbohydrate solutions (see FIG. 7) and in the carbohydrate solutions (FIGS. 4 and 5) were compared to photomicrographs of a section of normal rat liver (FIG. 1) and sections of rat liver allografts stored for 8 hours at 1° C. in solutions containing normal saline and 2 mM calcium chloride (FIG. 2). FIG. 2 shows the well developed injury with rounding and detachment of endothelial cells.

Figure 7:
FIG. 7 is a photomicrograph of a section of a rat liver allograft stored for 8 hours at 1° C. in a solution containing isothionate 100 mM (Isothionate 1 solution, Table III) (original magnification ×400, H and E stain)

Following 8 hours of storage, livers stored in solutions based on non-carbohydrates all had mean increases in weight of several per cent. The lobular architecture of these livers was well maintained. Hepatocytes had variable degrees of peripheral vacuole formation and blebs were readily visible in the sinusoidal lumina. SLC had round, darkly-staining, pyknotic nuclei, and were also usually detached from the underlying substratum providing only moderate improvement in the picture shown in FIG. 2. FIG. 7 provides a representative example of the effect of these noncarbohydrate solutions.

Figure 3:
FIG. 3 is a photomicrograph of a section of a rat liver allograft stored for 8 hours at 1° C. in a solution containing lactobionate at a concentration of 100 mM (Lactobionate 1 solution, Table III) (original magnification ×400, H and E stain)
Figure 4:
FIG. 4 is a photomicrograph of a section of a rat liver allograft stored for 8 hours at 1° C. in a solution containing glucuronate, at a concentration of 100 mM (Glucuronate 1 solution, Table III) (original magnification ×400, H and E stain)

Livers stored in carbohydrate based solutions had mean weight losses of several per cent. Hepatocytes showed only rare vacuole and bleb formation, and most SLC were attached, although swollen and even round and darkly-staining. Some detached cells could be seen (FIG. 3 and 4). In particular, FIG. 3 showed marked improvement in preservation when compared to FIG. 2, with only minor detachment and rounding of endothelial cells. FIG. 4 showed even better preservation than FIG. 3 with only very minor changes.

These comparisons revealed that regardless of Na:K ratio, magnesium concentration, or anion concentration, livers stored in solutions based on carbohydrate anions were associated with weight loss and a moderate degree of injury to SLC after 8 hours of cold storage, while those stored in noncarbohydrate anioncontaining solutions gained weight and demonstrated more severe microvascular injury histologically. Among livers stored in solutions based on carbohydrate anions, the degree of liver weight gain did not relate to the morphologic appearance of the microcirculation.

B. Comparison of Various Carbohydrate Anions in Preservation Solutions

Five different comparisons were used to identify the carbohydrate anion whose inclusion in preservation solutions provided the best preservation of the microcirculation as determined by the screening test. Solutions based on galacturonate, gluconate, lactobionate, glucoheptonate, glucuronate, and saccarate were evaluated.

Livers stored for 8 hours in solutions based on galacturonate, lactobionate (lactobionate 2) and saccarate (see Table III for compositions of solutions) were compared. All contained MgSO4 5 mM, similar ratios of Na:K, impermeant anion concentration of 100 mM (except saccarate) and had final osmolalities of approximately 300 mOsm/1. Saccarate was employed at a concentration of 85 mM because its valence of 2 mandated high cation concentrations. Livers stored in the galacturonate, lactobionate 2 and saccarate solutions had changes in liver weight of −1.2, 9.6% and −3.36% respectively.

Galacturonate provided significant protection of the microcirculation. After 8 hours of storage in the galacturonate solution, lobular architecture was well preserved and hepatocytes looked quite normal with few vacuoles or blebs. SLC were swollen, but the majority remained attached. Those that were detached appeared swollen and rounded rather than truly pyknotic. In some areas, normal, flat SLC could be seen. Livers stored in the lactobionate 2 solution had normal appearing hepatocytes. SLC at all stages of injury were present. Some appeared normal, flat and elongated, some were swollen and others were detached with round, dark, pyknotic nuclei. This appearance is typical of livers stored to the limit of viability, as determined in a previous study of saline-preserved livers (McKeown, C. M. B. et al, Transplantation 46:178, 1988). SLC of livers stored in the saccarate solution, although not entirely comparable because of the reduced concentration of saccarate used, were less well preserved than those of livers stored in solutions based on galacturonate or lactobionate. Most were round with darkly-staining nuclei, and frequently were attached to the substratum over a small area of the cell surface. Occasional swollen attached SLC were seen. Hepatocytes were normal and vacuoles and blebs were rare.

Livers stored in solutions based on gluconate, glucuronate and lactobionate (solutions gluconate 2, glucuronate 1 and lactobionate 1 in Table III) were compared. All solutions contained MgSO$_4$ 40 mM, a final osmolality of 300 mOsm/1, an impermeant anion concentration of 100 mM and a Na:K ratio of 46:54. Mean changes in liver weight after 8 hours of cold storage were −1.5, −8.0 and −5.6% respectively. Livers stored in the gluconate 2 solution had well preserved hepatocytes with blebs and vacuoles visible only in some sections. A variable degree of microvascular injury was noted ranging from a typical picture of reversible injury with swollen but attached SLC and few detached cells, to predominately detached cells with round, darkly-staining, pyknotic nuclei. Livers stored in the glucuronate 1 solution were notably superior (FIG. 4). Hepatocytes were wellpreserved, and frequency had a granular cytoplasm, an appearance noted in an earlier study after preservation in UW solution (Holloway, C.M.B., Transplantation 48:179–182, 1989). SLC were generally swollen, but all were attached, and flat; elongated cells were frequently seen. Livers preserved in the lactobionate 1 solution were associated with normal appearing hepatocytes and few blebs or vacuoles. Sinusoidal cells were almost all attached to the underlying substratum. Many were simply swollen, but a significant number were round, with darkly-staining pyknotic nuclei (FIG. 3). This comparison clearly implicated an advantage to glucuronate over gluconate or lactobionate in the protection against microvascular injury.

EXAMPLE 2

The efficacy of solutions based on lactobionate was compared with those based on glucuronate. Comparisons were made of solutions containing the principal electrolytes found in UW solution and solutions which are isosmolar glucuronate. Comparisons were also made of the lactobionate 1 solution and glucuronate 1 solution, and of the lactobionate 3 and glucuronate 5 solution. See Table III for composition of test solutions.

Figure 5:
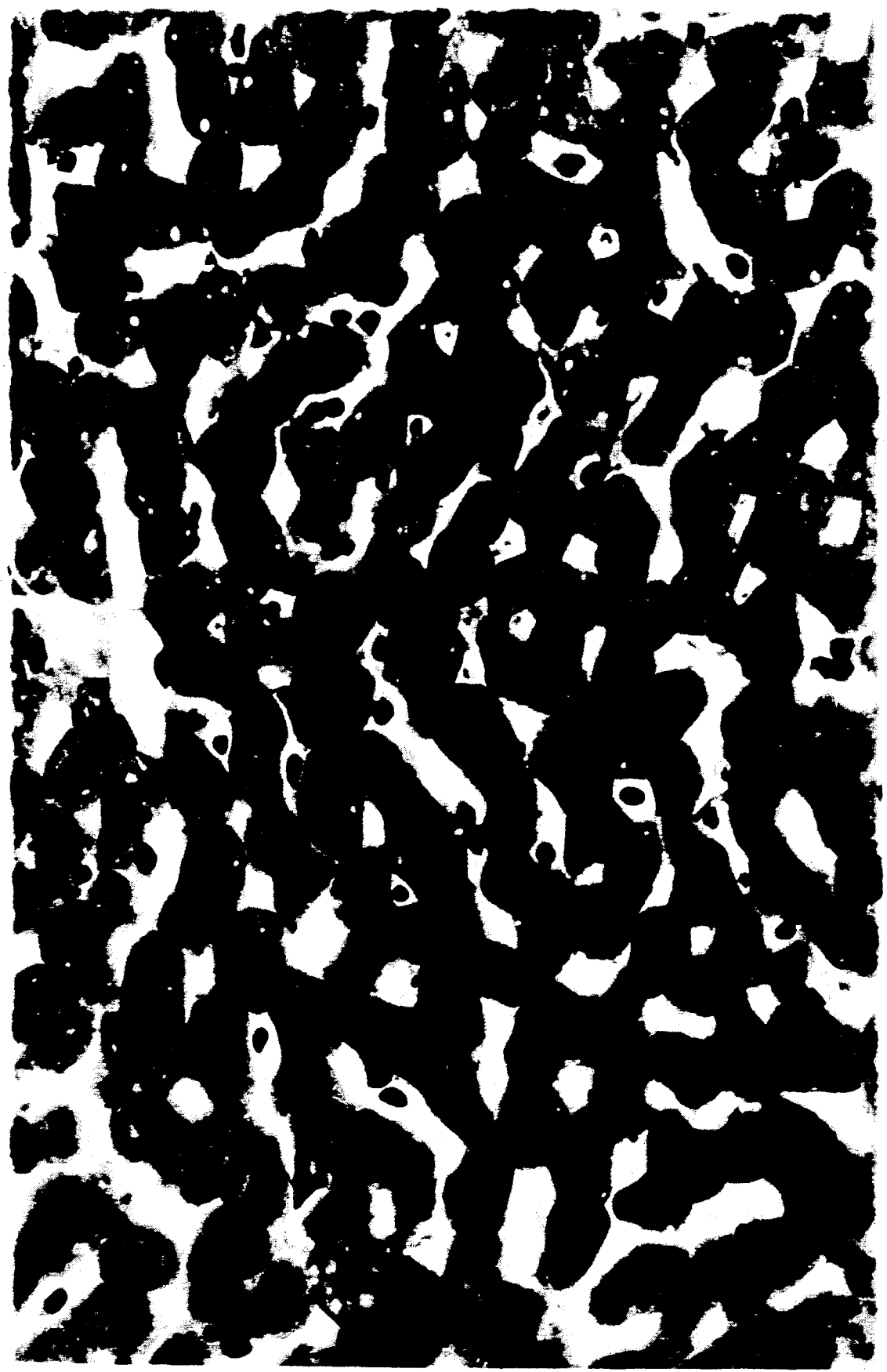
FIG. 5 is a photomicrograph of a section of a rat liver allograft stored for 16 hours at 1° C. in a solution containing lactobionate 100 mM (Lactobionate 1 solution, Table III) (original magnification ×400, H and E stain)
Figure 6:
FIG. 6 is a photomicrograph of a section of a rat liver allograft stored for 16 hours at 1° C. in a solution containing glucuronate at a concentration of 100 mM (original magnification ×400, H and E stain)

Histologically, livers stored for 8 hours in these solutions had a similar appearance. Lobular architecture was well preserved, and hepatocyte blebs and vacuoles were rare. Almost all SLC were attached, but swollen, or rarely round and pyknotic. Occasional elongated, flat cells were observed. Similarly, after 16 hours of cold storage, little difference could be discerned, although review of blinded slides by two independent observers consistently noted slight but definitely superior preservation with glucuronate. FIG. 5 shows substantial injury to the endothelial lining with rounding and detachment of endothelial cells. FIG. 6 shows less injury to the endothelium than in FIG. 5. Architecture was well preserved and bleb and vacuoles were prominent. Severe microvascular injury was present with most SLC rounded with darkly-staining pyknotic nuclei. Many were detached, and others were attached to the substratum over a small area of the cell surface. The SLC injury seen in these livers was less than that seen after storage for 8 hours in NaCl 0.9% and CaCl$_2$ 2mM (FIG. 2).

EXAMPLE 3

The superior protection of the microcirculation provided by solutions containing 100 mM glucuronate over solutions based on noncarbohydrate, or even other carbohydrate anions prompted the evaluation of livers stored in similar solutions but with different concentrations of glucuronate. Livers were stored for 16 hours in solutions containing 100 mM glucuronate (Glucuronate I, Table III), 140 mM glucuronate (Glucuronate 2, Table III), and 200 mM glucuronate (Glucuronate 3, Table III). The 200 mM Glucuronate solution was mannitol free and had an osmolality of 366 mOsm./1. The Na:K ratio in all solutions was 46:54.

All livers stored in glucuronate based solutions lost weight during storage. The change in weight of livers stored in the solutions containing 100, 140, and 200 mM Glucuronate for 8 hours at 4° C. was −7.1, −5.29 and −4.5% respectively and after 16 hours was −11.2%, −12.2 and −6.6% respectively.

The histology of livers stored in the 100 mM and 140 mM glucuronate solutions were quite similar whereas livers stored in the 200 mM solution showed deterioration in the morphology of the sinusoidal lining cells.

EXAMPLE 4

Liver functions in livers stored in UW solution and a solution containing glucuronate (GUW) were studied using the isolated perfused rat liver technique as described in S. Iu, P.R.C. Harvey et al, 1987, Transplantation 44(4):562. The glucuronate solution (GUW) was prepared as follows 19.41 grams of glucuronic acid (Sigma) was added to 400 ml of distilled and deionized water at room temperature (20° to 24° C.) and mixed until the solution was clear of undissolved material. 20 ml of 5N KOH solution, 4.0 ml of 5N NaOH solution, 1.34 grams of adenosine, 0.135 grams of allopurinol, 3.4 grams of potassium phosphate monobasic, 0.60 grams anhydrous magnesium sulfate, 17.83 grams of raffinose, 0.92 grams of glutathione and 500 ml hydroxyethyl starch (pentastarch) were each added to the mixture and the mixture was stirred after the addition of each constituent until the constituent was dissolved. The pH of the solution was then adjusted to pH 7.4±0.1 with 5N NaOH. The volume was adjusted to 1 liter and the solution was stirred for 5 minutes. The UW solution was prepared by the same procedure but lactobionic acid (35.83 g/1) replaced the glucuronic acid.

Figure 8:
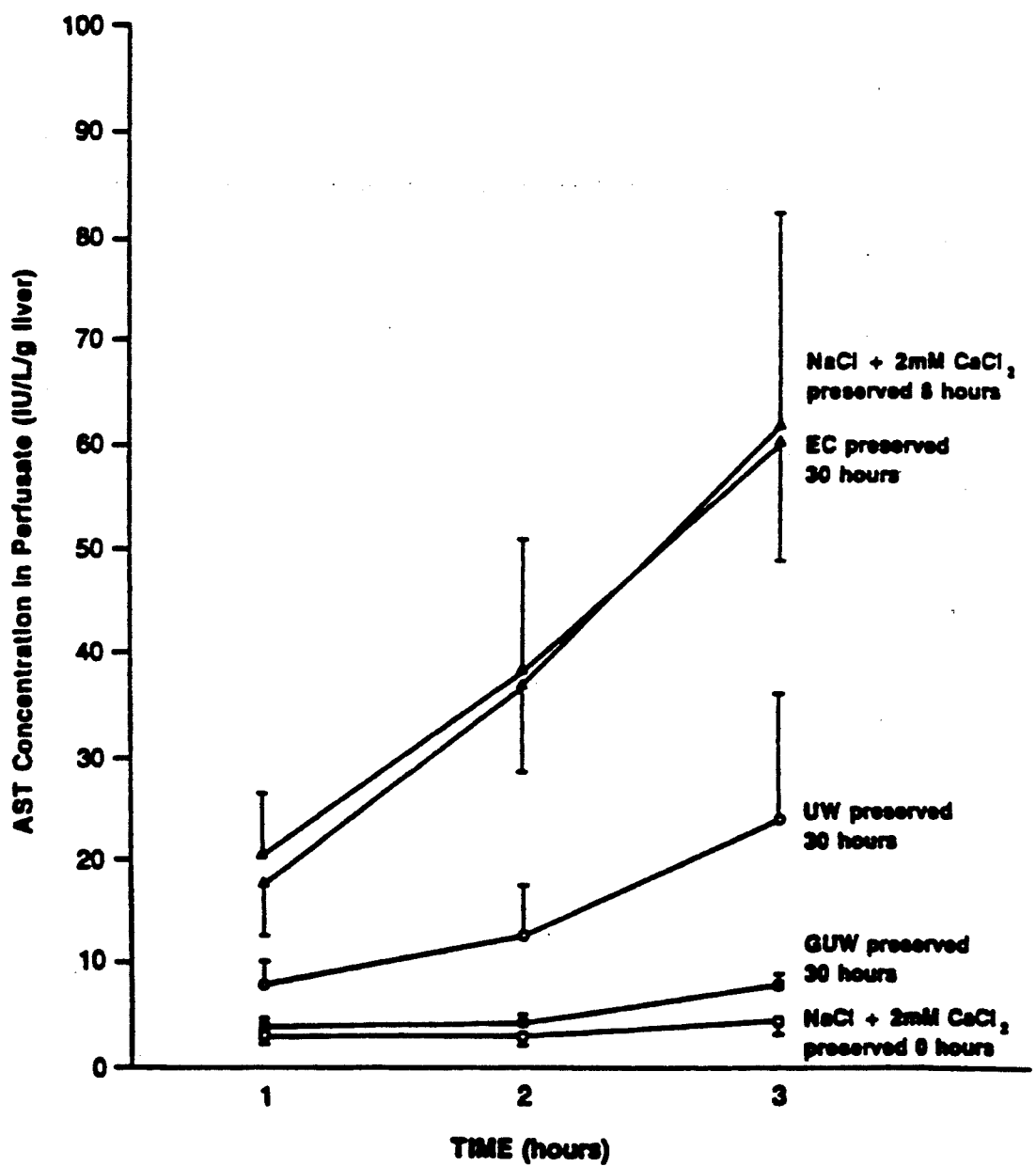
FIG. 8 is a graph showing AST concentration (mean±SEM) in perfusate of isolated perfused rat liver (IPRL) reperfused for 3 hours at 37° C. after preservation in UW solution for 30 hours at 1° C. or for 30 hours at 1° C. in a UW based solution in which lactobionate was substituted by glucuronate on an equimolar basis (GUW); after no preservation (NaCl—2 mM $CaCl_2$ preserved 6 hours); preservation in Eurocollins solution (EC) for 30 hours; and, preservation in normal saline and 2 mM $CaCl_2$ for 8 hours.
Figure 9:
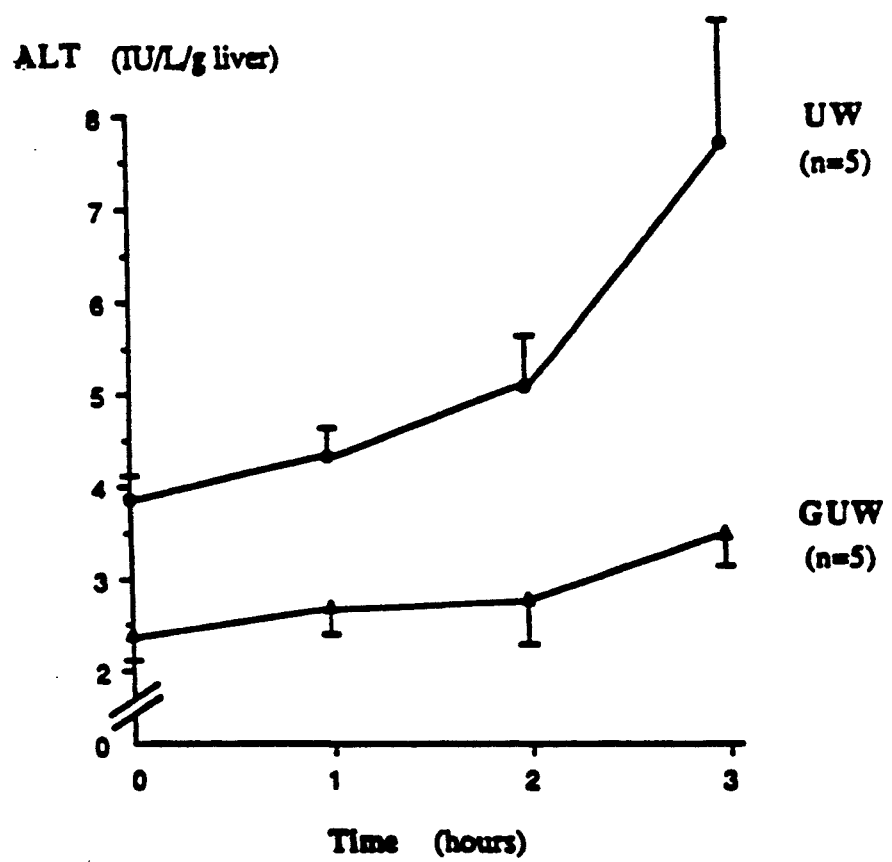
FIG. 9 is a graph showing ALT concentration (mean±SEM) in perfusate of isolated perfused rat liver (IPRL) reperfused for 3 hours at 37° C. (a) after preservation in UW solution for 30 hours at 1° C., or for 30 hours at 1° C. in a UW based solution in which lactobionate was substituted by glucuronate on an equimolar basis (GUW); after no preservation (NaCl—2 mM $CaCl_2$ preserved 6 hours); preservation in Eurocollins solution (EC) for 30 hours; and, preservation in normal saline and 2 mM $CaCl_2$ for 8 hours.
Figure 10:
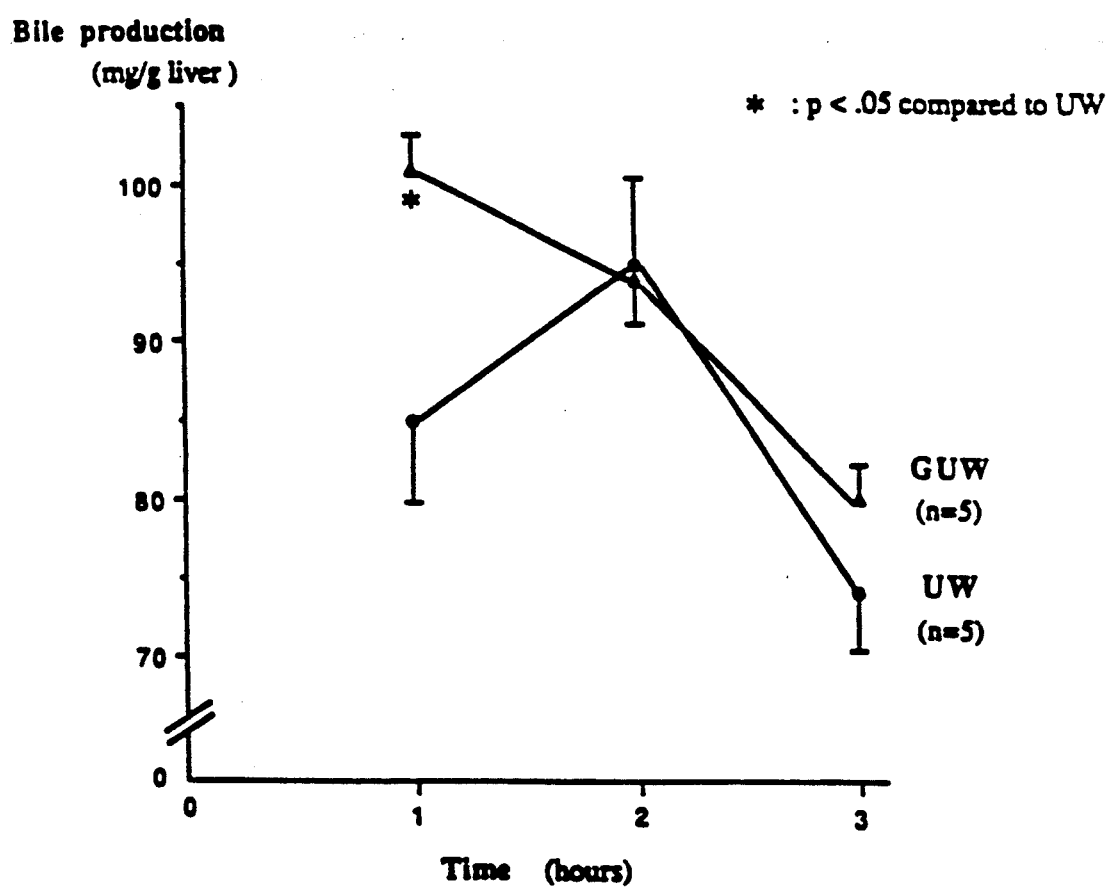
FIG. 10 is a graph showing bile production (mean ±SEM) in perfusate of isolated perfused rat liver (IPRL) reperfused for 3 hours at 37° C. after preservation in UW solution for 30 hours at 1° C. or for 30 hours at 1° C. in a UW based solution in which lactobionate was substituted by glucuronate on an equimolar basis (GUW); after no preservation (NaCl—2 mM CaCl$_2$ preserved 6 hours); preservation in Eurocollins solution (EC) for 30 hours; and, preservation in normal saline and 2 mM CaCl$_2$ for 8 hours.
Figure 11:
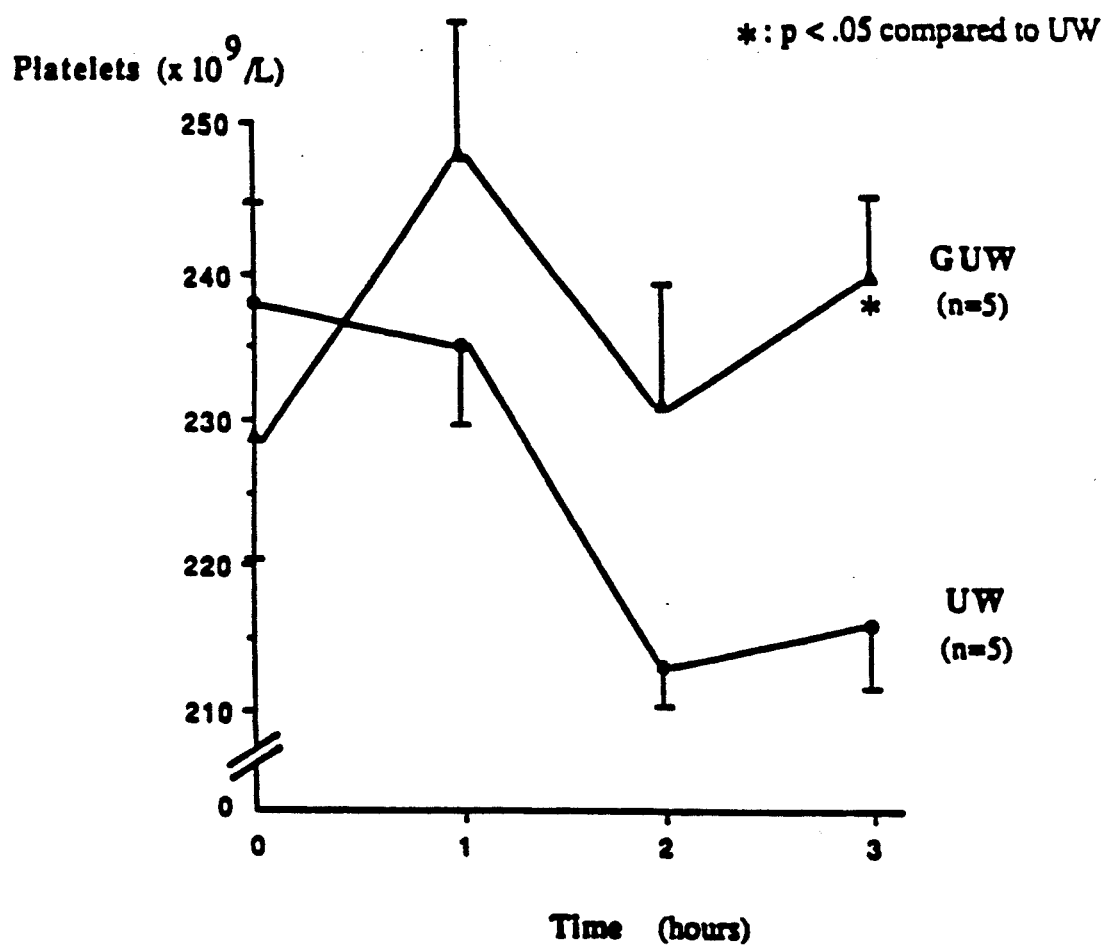
FIG. 11 is a graph showing platelet concentration (mean ±SEM) in perfusate of isolated perfused rat liver (IPRL) reperfused for 3 hours at 37° C. after preservation in UW solution for 30 hours at 1° C., or UW for 30 hours at 1° C. in a UW based solution in which lactobionate was substituted by glucuronate on an equimolar basis (GUW); after no preservation (NaCl—2 mM CaCl$_2$ preserved 6 hours); preservation in Eurocollins solution (EC) for 30 hours; and, preservation in normal saline and 2 mM CaCl$_2$ for 8 hours.

Four liver function tests, namely AST (aspartate aminotransferase), and ALT (alanine aminotransferase) concentrations in perfusate, perfusate platelet count and bile flow were used in the study. Livers were preserved for 30 hours at 1° C. in UW or GUW and then reperfused on the isolated perfused rat liver system at 37° C. for 3 hours. AST and ALT were measured using commercially available kits (Boehringer Mannheim). The results of the liver function tests are shown in FIG. 8 (AST), FIG. 9 (ALT), FIG. 10 (Bile flow) and FIG. 11 (platelet count) and summarized in Table IV.

Livers stored in GUW showed marked and statistically improved function in AST and ALT release during the reperfusion period. The present inventors have previously shown that AST release is closely related to transplant viability in this model (Iu S., Transplantation 44: 562, 1987). The reduced release of the transaminases AST and ALT signifies reduced liver cell injury in the GUW group. Toledo-Pereyra et al. (Ann Surg, 181: 289, 1975) have also found that the results of auxiliary transplantation were best when no increases in AST occurred during perfusion. There was also a significant reduction in the platelet count in the UW group but not in the GUW group. This signifies that there is less microvascular injury in the GUW group, a conclusion supported by the morphological studies described above. Finally bile flow was better in the GUW group although in this paramenter statistical significance was not quite achieved. The results suggest that allografts preserved in the GUW solution containing glucuronate have greater transplantation viability than allografts preserved in UW solution.

The present invention has been described in detail and with particular reference to the preferred embodiments; however, it will be understood by one having ordinary skill in the art that changes can be made thereto without departing from the spirit and scope thereof.

TABLE I

Composition of Known Preservation Solutions

|  | Collins-2* g/l | Sacks-2* g/l | Belzer* Perfusate g/l |
|---|---|---|---|
| $KH_2PO_4$ | 2.0 | 4.16 | 3.4 |
| $K_2HPO_4 3H_2O$ | 9.7 | 9.70 | — |
| KCl | 1.12 | — | — |
| $KHCO_3$ | — | 2.30 | — |
| Mannitol | — | 37.5 | — |
| Glucose | 25 | — | 1.5 |
| $MgSO_4/7H_2O$ | 7.38 | — | 8 |
| $MgCl_2$ | — | (2 meq/ml) | — |
| Adenosine | — | — | 1.3 |
| Sodium | — | — | 17.5 |
| Glutathione |  |  |  |
| Albumin | — | — | 5.3 |
| $NaHCO_3$ | 0.84 | 1.26 | — |
| Allopurinol | — | — | 0.113 |
| Verapamil | — | — | — |
| $K^+$- | — | — | — |
| Lactobionate |  |  |  |
| Citrate |  |  |  |
| Raffinose | — | — | — |
| Hydroxyethyl starch | — | — | — |
| Osmolality (mOsm/Kg) | 320 | 430 | 300 |
| pH | 7.00 | 7.00 | 7.10 |

*Compositions taken from U.S. Pat. No. 4,920,044, column 5, line 48 to column 6, line 13.

|  | U.S. Pat. No. 4,920,004 g/l | Marshall's Isotonic Citrate* (mM) | UW** g/l |
|---|---|---|---|
| $KH_2PO_4$ | 1.54–2.56 |  | 3.4 |
| $K_2HPO_4 3H_2O$ | 7.38–12.2 |  | — |
| KCl | 0.84–1.40 |  | — |
| $KHCO_3$ | 0.63–1.05 |  | — |
| Mannitol | 0–2.87 | 100 | — |
| Glucose | 20–37 |  | — |
| $MgSO_4/7H_2O$ | 0.0–4.62 or | 40 | 1.23 |
| $MgCl_2$ | 0.0–0.4 meq/ml | 0.3 | — |
| Adenosine | 0.75–1.25 |  | 1.34 |
| Sodium | — |  | 0.92 |
| Glutathione |  |  |  |
| Albumin | — |  | — |
| $NaHCO_3$ | 0.63–1.05 |  | — |
| Allopurinol | 0–0.125 |  | 0.136 |
| Verapamil | 0–1.0 |  | — |
| $K^+$- | — | — | 35.83 |
| Lactobionate |  |  |  |
| Citrate |  | 56 |  |
| Raffinose | — | — | 17.83 |
| Hydroxyethyl starch | — | — | 50 |
| Osmolality | 255–425 | 300 mOsm/l | 320–330 mOsm/kg |

TABLE I-continued

Composition of Known Preservation Solutions

|  |  |  |  |
|---|---|---|---|
| pH | mOsm/kg 7.20–7.50 | 7.1 | 7.40 |

*Composition taken from Holloway et al., Transplantation 48:179, at 180, 1989
**Composition obtained from Folkert D. Belzer and James H. Southard, University of Wisconsin.

TABLE II

|  | Concentration mM |
|---|---|
| Glucuronate (as sodium or potassium salt) | 3–200 |
| $KH_2PO_4$ | 5–40 |
| $MgSO_4$ | 1–50 |
| Raffinose | 5–50 |
| Adenosine | 1–50 |
| Allopurinol | 0.5–5 |
| Glutathione | 1–10 |
| Hydroxyethyl Starch | 10–70 g/l |
| Insulin | 0–100 U/l |
| Bactrim | 0–1.0 ml/l |
| Dexamethasone | 0–12 mg/l |

TABLE III

Composition of Test Preservation Solutions*

| Composition | | Concentration mM | Conc. in g/l |
|---|---|---|---|
| Cation | Anion |  |  |
| Name of Solution Butyrate 1 | | | |
| Sodium | Butyrate | 140 | 15.414 |
| Magnesium | Sulphate | 5 | 1.232 |
| Uncharged solutes Mannitol | | 25 | 4.55 |
| Osmolality: 300. | | | |
| Name of Solution Alpha-hydroxy butyrate | | | |
| Sodium | Alpha-hydroxy butyrate | 140 | 17.654 |
| Magnesium | Sulphate | 5 | 1.232 |
| Uncharged solutes Mannitol | | 23 | 4.19 |
| Osmolality: 300. | | | |
| Name of Solution Gamma-hydroxy butyrate | | | |
| Sodium | Gamma-hydroxy butyrate | 140 | 17.654 |
| Magnesium | Sulphate | 5 | 1.232 |
| Uncharged solutes Mannitol | | 28 | 5.10 |
| Osmolality: 300. | | | |
| Name of Solution Galacturonate | | | |
| Sodium | Hydroxide | 46 |  |
| Potassium | Hydroxide | 54 | 3.03 |
| Hydrogen | Galacturonate (Galacturonic Acid) | 100 | 21.22 |
| Magnesium | Sulphate | 5 | 1.232 |
| Uncharged solutes Mannitol | | 115 | 20.95 |
| Osmolality: 300. | | | |
| Name of Solution Glucoheptonate | | | |
| Sodium | Glucoheptonate | 140 | 38.5 |
| Magnesium | Sulphate | 5 | 1.232 |
| Uncharged solutes Mannitol | | 50 | 9.11 |
| Osmolality: 300. | | | |
| Name of Solution Gluconate 1 | | | |
| Sodium | Gluconate | 37 | 8.069 |
| Potassium | Gluconate | 19 | 4.450 |
| Magnesium | Sulphate | 40 | 9.859 |
| Potassium | Chloride | 25 | 1.865 |
| Uncharged solutes Mannitol | | 100 | 18.22 |
| Osmolality: 302. | | | |
| Name of Solution Gluconate 2 | | | |
| Sodium | Gluconate | 46 | 10.032 |
| Potassium | Gluconate | 54 | 12.646 |
| Magnesium | Sulphate | 40 | 9.859 |
| Uncharged solutes | | 70 | 12.75 |

TABLE III-continued

Composition of Test Preservation Solutions*

| Composition Cation | Anion | Concentration mM | Conc. in g/l |
|---|---|---|---|
| Mannitol | | | |
| Osmolality: 300. | | | |
| *Name of Solution Gluconate 3* | | | |
| Sodium | Gluconate | 46 | 10.032 |
| Potassium | Gluconate | 54 | 12.646 |
| Magnesium | Sulphate | 5 | 1.232 |
| Uncharged solutes | | 105 | 19.13 |
| Mannitol | | | |
| Osmolality: 300. | | | |
| *Name of Solution Gluconate 4* | | | |
| Sodium | Gluconate | 100 | 21.81 |
| Magnesium | Sulphate | 5 | 1.232 |
| Uncharged solutes | | 105 | 19.13 |
| Mannitol | | | |
| Osmolality: 301 | | | |
| *Name of Solution Glucuronate 1* | | | |
| Sodium | Glucuronate | 46 | 10.764 |
| Hydrogen | Glucuronate (Glucuronic Acid) | 54 | 10.481 |
| Potassium | Hydroxide | 54 | 3.03 |
| Magnesium | Sulphate | 40 | 9.859 |
| Uncharged solutes | | 77 | 14.03 |
| Mannitol | | | |
| Osmolality: 301 | | | |
| *Name of Solution Glucuronate 2* | | | |
| Sodium | Glucuronate | 64 | 14.98 |
| Hydrogen | Glucuronate (Glucuronic Acid) | 76 | 14.74 |
| Potassium | Hydroxide | 76 | 4.26 |
| Magnesium | Sulphate | 5 | 1.23 |
| Uncharged solutes | | 36 | 7.29 |
| Mannitol | | | |
| Osmolality: 301 | | | |
| *Name of Solution Glucuronate 3* | | | |
| Sodium | Glucuronate | 92 | 21.54 |
| Hydrogen | Glucuronate (Glucuronic Acid) | 108 | 20.96 |
| Potassium | Hydroxide | 108 | 6.04 |
| Magnesium | Sulphate | 5 | 1.23 |
| Osmolality: 366 | | | |
| *Name of Solution Glucuronate 4* | | | |
| Sodium | Glucuronate | 140 | 32.77 |
| Magnesium | Sulphate | 5 | 1.23 |
| Uncharged solutes | | 36 | 7.29 |
| Mannitol | | | |
| Osmolality: 300 | | | |
| *Name of Solution Glucuronate 5* | | | |
| Sodium | Glucuronate | 120 | 28.09 |
| Potassium | Hydrogen Phosphate | 25 | 3.40 |
| Magnesium | Sulphate | 5 | 1.23 |
| Uncharged solutes | | | |
| Osmolality: 330 | | | |
| *Name of Solution Isothionate* | | | |
| Sodium | Isothionate | 100 | 14.81 |
| Magnesium | Sulphate | 5 | 1.23 |
| Uncharged solutes | | 104 | 18.49 |
| Mannitol | | | |
| Osmolality: 306. | | | |
| *Name of Solution Lactobionate 1* | | | |
| Hydrogen | Lactobionate (Lactobionic Acid) | 46 | 16.48 |
| Sodium | Hydroxide | 46 | 1.84 |
| Hydrogen | Lactobionate (Lactobionic Acid) | 54 | 19.30 |
| Potassium | Hydroxide | 54 | 3.03 |
| Magnesium | Sulphate | 40 | 9.85 |
| Uncharged solutes | | 72 | 13.13 |
| Mannitol | | | |
| Osmolality: 305 | | | |
| *Name of Solution Lactobionate 2* | | | |
| Hydrogen | Lactobionate (Lactobionic Acid) | 46 | 16.48 |
| Sodium | Hydroxide | 46 | 1.84 |
| Hydrogen | Lactobionate (Lactobionic Acid) | 54 | 19.30 |
| Potassium | Hydroxide | 54 | 3.03 |
| Magnesium | Sulphate | 5 | 1.23 |
| Uncharged solutes | | 108 | 19.64 |
| Mannitol | | | |
| Osmolality: 310 | | | |
| *Name of Solution Lactobionate 3* | | | |
| Sodium | Lactobionate | 120 | 43.00 |
| Potassium | dihydrogen phosphate | 25 | 3.40 |
| Magnesium | Sulphate | 5 | 1.23 |
| Uncharged solutes | | | |
| Glutathione | | 3 | 0.9212 |
| Raffinose | | 30 | 17.83 |
| Osmolality: 326 | | | |
| *Name of Solution Proprionate* | | | |
| Hydrogen | Proprionate (Proprionic Acid) | 54 | |
| Potassium | Hydroxide | 54 | 3.03 |
| Sodium | Proprionate | 46 | 4.42 |
| Magnesium | Sulphate | 5 | 1.23 |
| Uncharged solutes | | 108 | 19.64 |
| Mannitol | | | |
| Osmolality: 300 | | | |
| *Name of Solution Saccarate* | | | |
| Potassium | Saccarate | 85 | 21.08 |
| Sodium | Hydroxide | 85 | 3.40 |
| Magnesium | Sulphate | 5 | 1.23 |
| Uncharged solutes | | 83 | 15.83 |
| Mannitol | | | |
| Osmolality: 326 | | | |

*The composition of these solutions is listed according to original ingredients. Anions and cations were often added as their respective acids and bases and titrated to neutrality. Therefore, to obtain final composition eliminate H+ and OH− as listed in the Table.

TABLE IV

| | Time | UW solution# | GUW solution# |
|---|---|---|---|
| $AST^a$ | 0 | 3.41 ± 0.83 | 1.46 ± 0.78* |
| | 60 | 8.11 ± 1.99 | 3.05 ± 1.28* |
| | 120 | 12.70 ± 4.93 | 3.76 ± 1.16* |
| | 180 | 23.97 ± 11.27 | 8.03 ± 1.13* |
| $ALT^a$ | 0 | 3.85 ± 0.60 | 2.40 ± 0.77* |
| | 60 | 4.34 ± 0.65 | 2.69 ± 0.60* |
| | 120 | 5.08 ± 1.30 | 2.77 ± 1.09* |
| | 180 | 7.72 ± 2.94 | 3.50 ± 0.82* |
| $Bile^a$ | 60 | 85 ± 11 | 101 ± 5* |
| | 120 | 95 ± 14 | 94 ± 6 |
| | 180 | 74 ± 12 | 80 ± 7 |
| $Plts^c$ | 0 | 238 ± 15 | 229 ± 17 |
| | 60 | 235 ± 14 | 248 ± 20 |
| | 120 | 213 ± 12 | 231 ± 18 |
| | 180 | 216 ± 9 | 240 ± 12 | means ± SD
*$p < 0.05$
$^a$IU/L/g liver
$^b$mg/g liver
$^c\times 10^9$/L

We claim:

1. A composition for the preservation and storage of organs intended for transplantation comprising an effective amount of glucuronic acid or a physiologically tolerated salt or ester thereof in a pharmaceutically acceptable organ preservation solution.

2. The composition as claimed in claim 1, wherein the pharmaceutically acceptable organ preservation solution has substantially the composition of UW solution.

3. The composition as claimed in claim 1, wherein the pharmaceutically acceptable organ preservation solution is UW solution modified such that it is devoid of potassium lactobionate.

4. The composition as claimed in claim 3, wherein the concentration of glucuronic acid or the physiologically tolerated salt or ester thereof is about 100–140 mM.

5. A composition for the preservation and storage of organs intended for transplantation, comprising a pharmaceutically acceptable preservation solution comprising:
   (a) between about 3–200 mM of the sodium or potassium salt of glucuronate;
   (b) between about 5–40 mM $KH_2PO_4$;
   (c) between about 1–50 mM $MgSO_4$;
   (d) between about 5–50 mM raffinose;
   (e) between about 1–50 mM adenosine;
   (f) between about 0.5–5 mM allopurinol;
   (g) between about 1–10 mM glutathione; and
   (h) between about 10–70 g/l hydroxyethyl starch.

6. The composition as claimed in claim 5, wherein the osmolality of the preservation solution is between about 270 and 330 mOsm/l.

7. The composition as claimed in claim 5, wherein the osmolality of the preservation solution is between about 320 and 330 mOsm/l.

8. A method for preserving and storing an organ intended for transplantation in a patient comprising infusing said organ with a composition comprising an effective amount of glucuronic acid or a physiologically tolerated salt or ester thereof in a pharmaceutically acceptable organ preservation solution.

9. The method as claimed in claim 8, wherein the pharmaceutically acceptable organ preservation solution has substantially the composition of UW solution.

10. The method as claimed in claim 8, wherein the pharmaceutically acceptable organ preservation solution is UW solution modified such that it is devoid of potassium lactobionate.

11. The method as claimed in claim 10, wherein the concentration of glucuronic acid or the physiological salt or ester thereof is about 100–140 mM.

12. The method for preserving and storing organs intended for transplantation in a patient comprising infusing said organs with a composition comprising a pharmaceutically acceptable preservation solution comprising:
   (a) between about 3–200 mM of the sodium or potassium salt of glucuronate;
   (b) between about 5–40 mM of $KH_2PO_4$;
   (c) between about 1–50 mM $MgSO_4$;
   (d) between about 5–50 mM raffinose;
   (e) between about 1–50 mM adenosine;
   (f) between about 0.5–5 mM allopurinol;
   (g) between about 1–10 mM glutathione;
   (h) between about 10–70 g/l hydroxyethyl starch.

13. The method as claimed in claim 12, wherein the osmolality of the preservation solution is between about 270 and 330 mOsm/l.

14. The method as claimed in claim 12 or 13, wherein the organ intended for transplantation is the liver.

15. The method as claimed in claim 12, wherein the osmolality of the preservation solution is between about 320 and 330 mOsm/l.

* * * * *